United States Patent [19]

Macher

[11] Patent Number: 5,545,654
[45] Date of Patent: Aug. 13, 1996

[54] PLEUROMUTILIN DERIVATIVES

[75] Inventor: Ingolf Macher, Wörgl, Austria

[73] Assignee: Biochemie Gesellschaft m.b.H., Tyrol, Austria

[21] Appl. No.: 178,317

[22] PCT Filed: Apr. 29, 1993

[86] PCT No.: PCT/EP93/01033

§ 371 Date: Jan. 3, 1994

§ 102(e) Date: Jan. 3, 1994

[87] PCT Pub. No.: WO93/22288

PCT Pub. Date: Nov. 11, 1993

[30] Foreign Application Priority Data

May 4, 1992 [AT] Austria ................... 897/92

[51] Int. Cl.⁶ .............. C07D 233/32; A61K 31/415
[52] U.S. Cl. .............. 514/392; 514/506; 548/324.1; 562/499
[58] Field of Search .............. 548/324.1; 514/392, 514/506; 562/499

[56] References Cited

U.S. PATENT DOCUMENTS 4,675,330  6/1987  Berner et al. ................ 514/365

FOREIGN PATENT DOCUMENTS

| 13768 | 8/1980 | European Pat. Off.. |
| 153277 | 9/1985 | European Pat. Off.. |
| 421364 | 4/1991 | European Pat. Off.. |

OTHER PUBLICATIONS

Fitzi, et al, *Tetrahedron* vol. 44, No. 17 pp. 5277–5292, (1988).

Kealy, et al, *J. Organic Chemistry*, vol. 26, No. 4, pp. 1097–1101 Apr., 1961.

Fitzi, et al, *Angew. Chem. Int. Ed. Engl.*, vol. 25, No. 4, 1986, pp. 345–346.

Smissman, et al, *J. Medicinal Chemistry*, vol. 19, No. 1, (1976), pp. 161–163.

Primary Examiner—Jacqueline Haley
Attorney, Agent, or Firm—Robert S. Honor; Melvyn M. Kassenoff; Thomas O. McGovern

[57] ABSTRACT

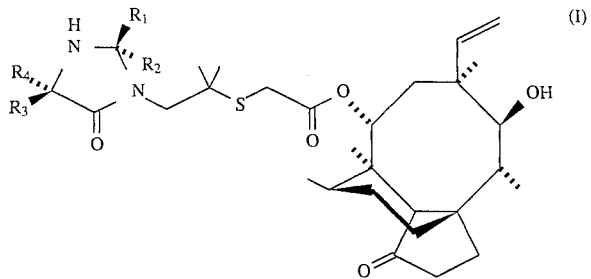

A compound of formula (I), in which each of $R_1$ and $R_2$ is independently hydrogen, alkyl or, together with the carbon atom to which it is bonded, a cycloalkyl; and each of $R_3$ and $R_4$ is independently hydrogen, alkyl or substituted alkyl. The compounds are useful intermediates and prodrugs.

14 Claims, No Drawings

PLEUROMUTILIN DERIVATIVES

This application is a National Stage Application of PCT/EP93/01033, filed Apr. 29, 1993, published as WO 93/22288, Nov. 11, 1993.

This invention concerns pleuromutilin derivatives that are useful as stable propleuromutilin antibacterial agents and that are useful in the production of pleuromutilin antibacterial agents.

Pleuromutilin compounds of the formula II

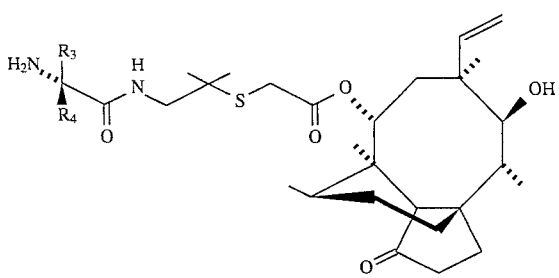

in which each of $R_3$ and $R_4$ is independently hydrogen, alkyl or substituted alkyl, are disclosed in European patent application EP 0 153 277. These compounds have useful biological properties; especially chemotherapeutic properties. For example the compounds of the formula II inhibit the growth of bacteria, Mycoplasms and Chlamydia and have antiparasitic properties (particularly against coccidia) and growth promoting activity. Hence these compounds can be used as medicaments and animal feeds.

However the compounds of the formula II could not previously be obtained in highly purified form since they are not available in crystalline form. As disclosed in EP 0 153 277, they could only be purified using chromatographic techniques.

Austrian Patent 392 272 discloses methods for the extraction and purification of compounds of the formula IV

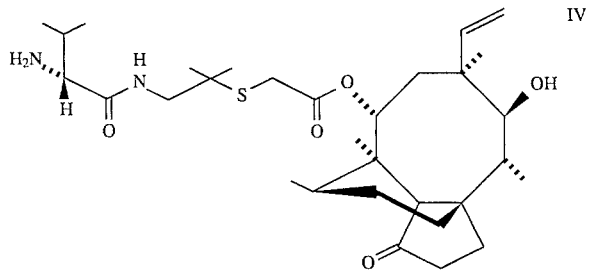

using specific solvents but analogous compounds with similar separation coefficients are not separated off and highly pure forms cannot be obtained.

Therefore there is a need for a route for preparing compounds of formula II that enables the compounds to be obtained in highly purified form (for example in crystalline form). There is also a need for stable compounds which may be used as pro-drugs for the compound of formula II.

Accordingly, in one aspect this invention provides compounds of the formula I

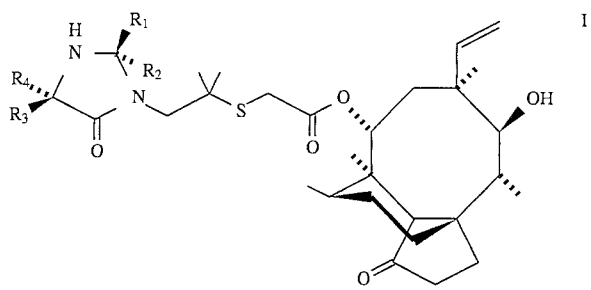

in which each of $R_1$ and $R_2$ is independently hydrogen, alkyl or, together with the carbon atom to which it is bonded, a cycloalkyl group; and each of $R_3$ and $R_4$ is independently hydrogen, alkyl or substituted alkyl. The compounds of the formula I are easily isolated in crystal form and hence are easily purified. Therefore the compounds of the formula I are useful intermediates in the production of compounds of the formula II in that they enable the preparation and isolation of highly purified forms of the compounds of formula II.

Preferably each $R_1$ and $R_2$ is independently H or $C_1$ to $C_6$ alkyl, or forms, together with the carbon atom to which it is bonded, a cycloalkyl ring of up to 6 carbon atoms (for example a 5 membered ring). $R_1$ and $R_2$ are both preferably methyl.

Preferably each $R_3$ and $R_4$ is independently H or $C_1$ to $C_6$ alkyl.

The invention also provides a process for the production of the compounds of the formula I comprising reacting a compound of formula II as defined above with a carbonyl compound of the formula III

in which $R_3$ and $R_4$ are as defined above, and isolating the compound of the formula I in tree base or acid addition salt form. The compound of formula I may be obtained in crystalline form.

The reaction may be carried out in a suitable solvent such as a lower alcohol (for example methanol, ethanol or isopropanol) or mixtures thereof.

The carbonyl compound of the formula III is preferably acetone, butan-2-one or cyclopentanone.

The invention also provides a method of producing compounds of the formula II as defined above in highly purified form (for example above 95% pure) comprising heating a compound of the formula I in the presence of an acid or a solvent, or both, and isolating the compound of the formula II in free base or acid addition salt form. Therefore, to produce compounds of the formula II in pure form, these compounds may be produced as conventionally produced to provide them in impure form. They may then be reacted with a carbonyl group of formula III as described above to provide the compounds of the formula I which may be readily purified since they are obtainable in crystalline form. The compounds of the formula I may then be convened to compounds of the formula II as described above.

Preferably the acid is a weak solution of hydrochloric acid or is a mixture of a solvent and a weak solution of hydrochloric acid.

The invention also provides the use of a compound of formula I as defined above in the preparation of compounds of the formula II in highly purified form.

The invention also provides a compound of the formula II in highly purified form (for example at least 95% and more preferably at least 98% pure).

The compounds of the formula I are extremely useful intermediates that enable the preparation of compounds of the formula II in highly purified form. However the compounds of the formula I are also useful as stable pro-drug forms of the compounds of the formula II because, at physiological pH's, they are released more slowly and in lower local concentrations. Also, they have lower basicity than the compounds of formula II and hence have better shelf-life.

Therefore the invention also provides a pharmaceutical composition comprising a compound of the formula I, as defined above, and a pharmaceutically acceptable carrier. Preferably the composition is in a form suitable for parenteral administration; for example as an injectable solution. Since the compounds of the formula I are hydrolysed slowly under physiological conditions and are released slowly, the pharmaceutical compositions act as retard forms of compositions that contain compounds of the formula II.

The compounds of the formula I may also be used as a stable form of the compounds of formula II in animal feeds. The imidazolidine moiety of the compounds of formula I is more stable against enzymatic hydrolysation than the corresponding moiety of the compounds of formula II. Hence feeds which contain the compounds of formula I are more resistant to decomposition caused by enzymes commonly found in animal feeds.

In use the effective dosage will vary depending upon the particular compound employed, the mode of administration, and the treatment desired. However satisfactory results as anti-bacteria is and anti-anaerobics can be obtained when the compounds are administered at a daily dosages similar to those described for compounds of the formula II in EP 0 153 277. If the compound is administered internally, the dosage form may contain the compound of formula I in admixture with a solid or liquid carrier or diluent.

For the prophylaxis of microorganism infections and for growth promotion in domestic animals, the dosage will vary depending upon the size and age of the animal and the effect desired. For example, for prophylactic treatment relatively low doses may be administered over a long time. Preferred doses in drinking water and foodstuffs are similar to those described for compounds of the formula II in EP 0 153 277. For pigs, it is preferred to administer the compound in foodstuffs. In this form, the compounds of the formula I are useful in the prophylactic treatment of swine dysentery.

Examples of the invention are now described, by way of example only. All temperatures are given in degrees centigrade.

Example 1 14-O-{[1-(2,2-Dimethyl-5(R)-isopropyl-imidazolidin-4-on-3-yl)-2-methyl-propan-2-yl]thioacetyl}mutilin 100 g of 14-O-{1-[(D)-2-amino-3-methylbutyrylamino]-2-methylpropan-2-yl-thioacetyl}mutilin hydrochloride are dissolved in 1000 ml water. 1000 ml tert.butylmethylether are added and the pH is adjusted to about 9 by the addition of 10N sodium hydroxide. The phases are then separated and the organic phase is washed twice with about 200 ml water. The tert.butylmethylether is distilled off and the residue is dissolved in ethanol. The ethanol is evaporated off and the residue collected. The residue is dissolved in 750 ml ethanol and 250 ml acetone and the mixture refluxed for 5 hours. Thereafter the mixture is left at room temperature for about 40 hours before being subjected to evaporation at 30° C. and under weak vacuum (about 120 m bar). About 650 ml of the ethanol/acetone solvent is evaporated off. The remaining crystal suspension is cooled with ice and stirred for an hour. The crystals are filtered, washed with cold ethanol and dried in a vacuum drier. The filtrate obtained from the filtration step is evaporated and the residue dissolved in 75 ml ethanol and 25 ml acetone. The mixture is left to stand for 48 hours at room temperature and the precipitate, in the form of crystals, then filtered off. The crystals are then washed with cold ethanol and dried in a vacuum drier. The dried crystals melt at a temperature of about 174° to 177 ° C.

Example 2 14-O-{[1-(2,2-Dimethyl-5(R)-isopropyl-imidazolidin-4-on-3-yl)-2-methyl-propan-2-yl]thioacetyl}mutilin 100 g of 14-O-{1-[(D)-2-amino-3-methylbutyrylamino]-2-methylpropan-2 -yl-thioacetyl}mutilin hydrochloride are dissolved in 1000 ml water. 1000 ml tert.butylmethylether are added and the pH is adjusted to about 9 to 10 by the addition of 10N sodium hydroxide. The phases are then separated and the organic phase is washed twice with about 200 ml water. The tert.butylmethylether is distilled off and the residue is dissolved in 200 ml acetone. The acetone is evaporated off and the residue collected. The residue is dissolved in 1000 ml acetone, 50 g of a 0.3 nm molecular sieve (obtained from Merck) is added and the mixture is refluxed for 27 hours. Thereafter the mixture is left at room temperature overnight. 3 g of activated charcoal is then added, the mixture is stirred for 5 minutes and is then filtered. The filtrate is evaporated at normal pressures to a volume of about 200 ml. Seeding crystals are then added to the clear solution and the solution stirred for an hour at room temperature and 2 hours in an ice bath. The precipitation is filtered off, washed with tert.butylmethylether and dried in a vacuum drier. The dried crystals melt at a temperature of about 174° to 177 ° C.

Example 3 14-O-{[1-(2,2-Dimethyl-5(R)-isopropyl-imidazolidin-4-on-3-yl)-2-methyl-propan-2-yl]thioacetyl}mutilin 150 g of 14-O -{1-[(D)-2-amino-3-methylbutyrylamino] -2-methylpropan-2 -yl-thioacetyl}mutilin hydrochloride are dissolved in 1500 ml water and the mixture stirred. 800 ml tert.butylmethylether are added and the pH is adjusted to about 9 by the addition of 10N sodium hydroxide. The phases are then separated and the organic phase is washed twice with about 500 ml water. 650 ml the tert.butylmethylether is evaporated off under normal pressure at temperature of 60°. The residue is dissolved in 186 ml acetone and 564 ml methanol and the mixture refluxed for 5 hours. Thereafter the mixture is left at room temperature for about 67 hours before being subjected to evaporation at 30° C. under vacuum. 450 ml isopropanol is added and the mixture stirred at room temperature for about 4 hours. The crystal suspension is cooled to about 0° and left over night. The crystals are filtered, washed with isopropanol and tert.butylmethylether, and dried in a vacuum drier. The dried crystals melt at a temperature of about 174° to 177° C.

Example 4 14-O-{[1-(2,2-Dimethyl-5(R)-isopropyl-imidazolidin-4-on-3-yl)-2-methyl-propan-2-yl]thioacetyl}mutilin The procedure set out in example 3 is followed except that the evaporation residue is dissolved in 480 ml methanol and 120 ml tert.butylmethylether instead of isopropanol. The dried crystals obtained melt at a temperature of about 174° to 177° C.

Example 5 14-O-{[1-(2,2-Dimethyl-5(R)-isopropyl-imidazolidin-4-on-3-yl)-2-methyl-propan-2-yl]thioacetyl}mutilin 1 g of 14-O-{1-[(L)-2-amino-3-methylbutyrylamino]-2-methylpropan-2-yl-thioacetyl}mutilin hydrochloride is dissolved in 10 ml water. 10 ml tert.butylmethylether are added and the pH is adjusted to about 9 to 10 by the addition of 10N sodium hydroxide to provide the compound in free base form. The phases are then separated and the organic phase is washed twice with water. The tert.butylmethylether is distilled off and the residue is dissolved in acetone. The acetone is evaporated off and the residue collected. The residue is dissolved in 10 ml acetone, 1 g of a 0.3 nm molecular sieve is added and the mixture is refluxed for 48 hours. Thereafter the mixture is filtered. The filtrate is evaporated in a rotary evaporator and the residue collected. The residue is dissolved in 2 ml acetone and seeding crystals are then added. After 2 hours at room temperature, the precipitation is filtered off, washed with tert.butylmethylether and dried in a vacuum drier. The dried crystals melt at a temperature of about 170° to 173° C.

Example 6
14-O-{[1-(2-ethyl-5(R)-isopropyl-2-methyl-imidazolidin-4-on-3-yl)-propan-2-yl]thioacetyl}mutilin A procedure analogous to that set out in example 2 is followed except that the evaporation residue is dissolved in methanol and, instead of acetone, 2-butanone is used. The dried crystals melt at a temperature of about 156° to 158° C.

Example 7
14-O-{[1-(5(R)-isopropyl-2,2-tetramethylene-imidazolidin-4-on-3-yl)-2-methyl-propan-2-yl]thioacetyl}mutilin A procedure analogous to that set out in example 6 is followed except that, instead of 2-butanone, cyclopentanone is used. The dried crystals melt at a temperature of about 130° to 132° C.

Example 8
14-O-{1-[(D)-2-amino-3-methylbutyrylamino]-2-methylpropan-2-yl-thioacetyl}mutilin hydrochloride 20 g of 14-O-{[1-(2,2-Dimethyl-5(R)-isopropyl-imidazolidin-4-on-3-yl)-2-methyl-propan-2-yl]thioacetyl}mutilin is dissolved in 80 ml water and 2.9 ml of 37% hydrochloric acid are added. The mixture is warmed to 90° for an hour. The clear solution is lyophilized or spray dried to provide the title compound in pure form (98% purity).

Example 9
14O-{1-[(D)-2-amino-3-methylbutyrylaminol-2-methylpropan-2-yl-thioacetyl}mutilin hydrochloride 10 g of 14-O-{[1-(2,2-Dimethyl-5(R)-isopropyl-imidazolidin-4-on-3-yl)-2-methyl-propan- 2-yl]thioacetyl}mutilin is dissolved in 100 ml methanol and 9.3 ml of 2N hydrochloric acid are added. The mixture is refluxed for about 1.5 hours and then dried in a rotary evaporator. The residue is dissolved in 50 ml water and the solution is lyophilized to provide the title compound in pure form (98% purity).

I claim:
1. A compound of formula I

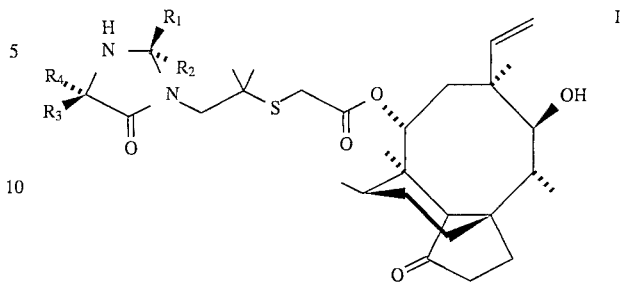

in which $R_1$ and $R_2$ are each independently hydrogen or $(C_{1-6})$alkyl, or together with the carbon atom to which they are attached form a cycloalkyl ring of up to 6 carbon atoms; and $R_3$ and $R_4$ are each independently hydrogen or $(C_{1-6})$ alkyl.

2. A compound according to claim 1 in which $R_1$ and $R_2$ are methyl.

3. A compound according to claim 1 which is 14-O-{[1-(2,2-dimethyl-5(R)-isopropyl-imidazolidin- 4-on-3-yl)-2-methylpropan-2-yl]thioacetyl }mutilin.

4. A compound of the formula I according to claim 1 in crystalline form.

5. A compound according to claim 1 which is 14O-{[1-(2-ethyl-5(R)-isopropyl-2-methyl-imidazolidin-4 -on-3-yl)-2-methylpropan-2-yl]thioacetyl}mutilin.

6. A compound according to claim 1 which is 14-O-{[1-(5(R)-isopropyl-2,2-tetramethylene-imidazolidin- 4-on-3-yl)-2-methylpropan-2-yl]thioacetyl}mutilin.

7. A pharmaceutical composition comprising an amount of a compound according to claim 1 effective for treating a microorganism infection and a pharmaceutically acceptable carrier therefor.

8. A pharmaceutical composition according to claim 7 in the form of an injectable solution for parenteral administration.

9. A pharmaceutical composition according to claim 7 in the form of an animal feed.

10. A method of treating a microorganism infection in a subject in need of said treatment, which comprises administering to the subject an amount of a compound according to claim 1 effective for the treatment of a microorganism infection.

11. A method according to claim 10 in which the microorganism infection is swine dysentery.

12. A process for preparing a compound of formula II

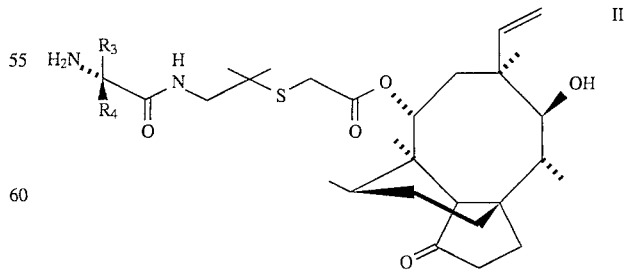

in which $R_3$ and $R_4$ are each independently hydrogen or $(C_{1-6})$alkyl, and having a purity of at least 95%, which comprises the steps of a) heating a compound of formula I

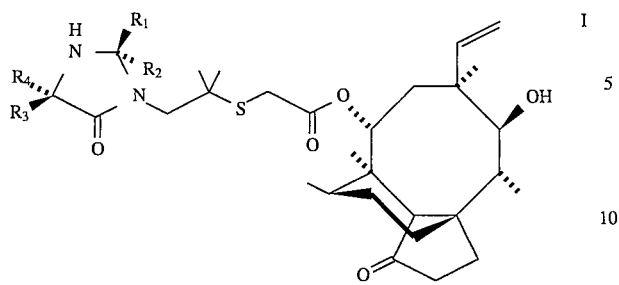

where $R_1$ and $R_2$ are each independently hydrogen or $(C_{1-6})$alkyl, or together with the carbon atom to which they are attached form a cycloalkyl ring of up to 6 carbon atoms, and $R_3$ and $R_4$ are as defined above, in the presence of an acid or an inert solvent or both; and b) isolating the compound of formula II in free base or acid addition salt form.

13. A process for preparing a compound of formula II

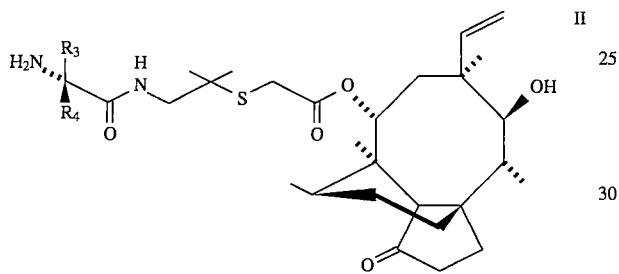

in which $R_3$ and $R_4$ are each independently hydrogen or $(C_{1-6})$alkyl, and having a purity of at least 95%, which comprises the steps of a) reacting a compound of formula II in impure form with a compound of formula III $$R_1-CO-R_2 \quad (III)$$

where $R_1$ and $R_2$ are each independently hydrogen or $(C_{1-6})$alkyl, or together with the carbon atom to which they are attached form a cycloalkyl ring of up to 6 carbon atoms, in an inert solvent to obtain a compound formula I

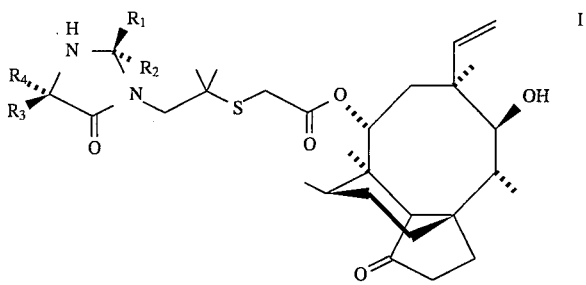

b) isolating the compound of formula I in pure free base or acid addition salt form;

c) heating the compound of formula I in the presence of an acid or an inert solvent or both; and d) isolating the compound of formula II in free base or acid addition salt form.

14. A process according to claim 13 which is carried out in a solvent selected from methanol, ethanol and isopropanol, and mixtures thereof.

* * * * *